United States Patent [19]

Scott et al.

[11] Patent Number: 4,678,663

[45] Date of Patent: Jul. 7, 1987

[54] HYDROQUINONE COMPOSITION HAVING ENHANCED BIO-AVAILABILITY AND PERCUTANEOUS ADSORPTION

[75] Inventors: Richard A. Scott, Burbank; Mitchell S. Wortzman, Los Angeles, both of Calif.; Eric Jungermann, Phoenix, Ariz.

[73] Assignee: Nuetrogena Corporation, Los Angeles, Calif.

[21] Appl. No.: 577,513

[22] Filed: Feb. 6, 1984

[51] Int. Cl.[4] .................. A61K 7/44; A61K 7/135; A61K 31/74

[52] U.S. Cl. .................. 424/62; 424/DIG. 5; 424/59; 424/60; 424/78; 514/169; 514/675; 514/725; 514/783; 514/847; 514/848; 514/886; 514/887

[58] Field of Search ............. 424/184, 331, 62, 59, 424/DIG. 5, 60

[56] References Cited

U.S. PATENT DOCUMENTS

| | | | |
|---|---|---|---|
| 4,122,029 | 10/1978 | Gee et al. | 252/309 |
| 4,264,586 | 4/1981 | Callingham et al. | 424/184 |
| 4,265,878 | 5/1981 | Keil | 424/184 |
| 4,280,994 | 7/1981 | Turney | 424/184 |
| 4,355,046 | 10/1982 | Süess | 424/355 |
| 4,421,769 | 12/1983 | Dixon et al. | 424/184 |
| 4,435,382 | 3/1984 | Shin | 424/66 |

FOREIGN PATENT DOCUMENTS

| | | | |
|---|---|---|---|
| 0142542 | 12/1978 | Japan | 424/184 |
| 0047606 | 4/1980 | Japan | 424/184 |
| 803289 | 10/1958 | United Kingdom | 424/184 |
| 1206790 | 9/1970 | United Kingdom | 424/184 |

OTHER PUBLICATIONS

Plein et al, Journal of the American Pharmaceutical Association, 2/1953, pp. 79 to 85.

*Primary Examiner*—Dale R. Ore
*Attorney, Agent, or Firm*—Richard M. Mybeck

[57] ABSTRACT

A new and improved vehicle for delivering pharmaceutical ingredients to the human skin in a manner whereby the bioavailability, subcutaneous adsorption, and effectiveness of the active ingredient are remarkably enhanced. The vehicle comprises a volatile silicone, a fatty alcohol having from 12-22 carbon atoms, a preselected active ingredient; and such preservatives or emulsifying agents as may be warranted.

8 Claims, No Drawings

HYDROQUINONE COMPOSITION HAVING ENHANCED BIO-AVAILABILITY AND PERCUTANEOUS ADSORPTION

INTRODUCTION

This invention relates to topical compositions and more particularly to a new and improved vehicle for delivering topically applied pharmaceutical and cosmetic ingredients in a manner whereby the bioavailability and effectiveness of the active ingredient is remarkably enhanced.

BACKGROUND

The prior art has traditionally delivered topically effective pharmaceutical agents in creams, lotions and gels, all of which require the user to soil his fingers and hands in the application of such medicaments and in the subsequent action of "rubbing it in". Further, such products are greasy, slow to dry and inevitably leave a residue which not only is visible, but rubs off onto clothing and the like, all of which are discomforting to the social ease of the user.

One variation from the traditional creams, lotions and gels occurred with the development of the so-called stick delivery systems which were used to apply antiperspirants, deodorants, lip balm, lip coloring and like ingredients which are generally applied to the surface of the skin.

Antiperspirant sticks based on the combination of a volatile silicone, a fatty alcohol and a powdered antiperspirant were recently developed and marketed. These sticks, however, have not been extended beyond simple antiperspirant sticks using water soluble inorganic antiperspirant salts. This limited use is the result of the known mechanism of antiperspirant vehicles and the need to intentionally design such delivery systems so as to limit the amount of active ingredient (antiperspirant) which can penetrate into the skin. For an antiperspirant to be efficacious, a large concentration of the active ingredient must be maintained on the surface of the skin from whence it is slowly dissolved and diffused into the apocrine ducts, rather than being absorbed through the skin. To extend this prior art to other pharmacologically active topical agents, it is necessary to greatly enhance the amount of the drug which is able to penetrate through the skin to reach the desired sites of action. This absorption of a drug through the skin is referred to as percutaneous absorption.

Nor does the typical lip balm formulation solve the problem because such products normally contain large amounts of wax (such as Beeswax, Carnauba, and the like), and oils, (such as, castor oil, lanolin and the like), whereupon a greasy/oily sensation is created on the skin which is not only unpleasant but gives the user the feeling of being "dirty". In addition, this type of formulation, as with antiperspirants, severely limits the percutaneous absorption of most drugs through the skin.

Likewise, the conventional creams and lotions fail to obviate the problems enumerated because the creams and lotions are excessively greasy and have the potential to sequester the active ingredient so that the percutaneous absorption of the drug and its efficacy is reduced.

Accordingly, one object of the present invention is to develope a consumer acceptable delivery system for applying pharmaceuticals and cosmetics to the human skin which avoids the aforesaid disadvantages of the prior art creams, lotions, gels and sticks while enabling the user to readily control its application to a specified location with maximum effectiveness, a minimum of waste, and no mess.

Another object of the present invention is to provide a silky and non-greasy delivery system which is capable of spreading a drug or cosmetic evenly and smoothly on the skin and which leaves virtually no residue.

A further object of the present invention is to provide a new and improved delivery system which is compatible with a broad range of dermatologically effective pharmaceuticals and is capable of delivering such pharmaceuticals with high efficiency and increased percutaneous absorption thereby increasing both the bioavailability of the active ingredient and its efficacy.

These and still further objects as shall hereinafter appear are fulfilled by the present invention in a remarkably unexpected fashion as will be readily discerned from a careful consideration of the detailed description of certain exemplary embodiments thereof which hereafter appear.

SUMMARY OF INVENTION

An improved delivery system for topically applied pharmaceutical and cosmetic ingredients whereby the bioavailability and percutaneous absorption of the active ingredient is remarkably enhanced, the "feel" of the product is pleasing to the user, it is simple and neat to use, and its compatibility enables a wide range of dermatologically active and cosmetically pleasing ingredients to be incorporated thereinto without any material depreciation of the unique properties accorded thereto.

DETAILED DESCRIPTION

The present invention relates to a semi-solid vehicle for applying a drug or cosmetic agent to the human skin and comprises a volatile silicone, such as dimethicone and cyclomethicone; a fatty alcohol having from 12 to 22 carbon molecules or a mixture of $C_{12}$ to $C_{22}$ fatty alcohols; a preselected active ingredient; and such preservatives, or emulsifying agents as may be warranted.

An important factor of the present invention is the use of a volatile silicone such as dimethicone, the cyclomethicones or equivalent cyclic silicones, which avoid the heavy oils and waxes heretofore employed and provide instead a silky and non-greasy lubricant which enables the active ingredient to be spread evenly and smoothly upon the skin. Once the active ingredient has been delivered to the selected site, the silicones will volatilize and leave no residue on the skin. Suitable silicones for use herein are available commercially from Dow Corning as 200 fluid (0.65 cs), 344 fluid (formerly Q2-1053) and 345 fluid (formerly F1-3597).

The use of Dodecanol, Tridecanol, Tetradecanol, Pentadecanol, Hexadecanol (cetyl alcohol), Heptadecanol Octadecanol, Nonadecanol, Eicosanol, Heneiconsanol, and Docosanol (Stearyl alcohol) or mixtures thereof provide another important feature of the invention.

Specifically the basic system of the present invention contains from about 20% up to about 40% (w/w) of fatty alcohol such as a mixture of stearyl and cetyl alcohol; from about 30% up to about 60% (w/w) volatile silicone such as dimethicone or a cyclomethicone; from about 0.1% up to about 10% (w/w) of an active drug or cosmetic reagent; and from about 1% to about 10% of various other ingredients such as preservatives, and/or emulsifying agents.

The system thus described has the further surprising advantage in that it is not limited just to water soluble drugs/cosmetics but can also be employed in a most propitious manner with many insoluble ingredients when suspended in a fine particulate form (less than about 30 μm) to form an acceptable product.

The specific details whereby our system is employed with specific pharmacological agents and cosmetic agents shall now be described. Special attention is directed to the ability of this system to stabilize a number of drug and cosmetic ingredients which are known to be unstable in most common vehicles, and to accept those active ingredients which heretofore have not been acceptable in any effective vehicle systems.

Active pharmaceutical ingredients which are effectively incorporated into the present delivery system and which, as will be demonstrated, exhibit improved stability, and enhanced bioavailability when appropriate, are listed in Table I. The accepted use of each ingredient and its expected shelf-life, as determined by accelerated stability studies, are also reported in Table I.

TABLE I

| INGREDIENT | USE | EXPECTED SHELF-LIFE* |
|---|---|---|
| Hydroquinone 2% | Skin Bleaching | 24-36 months |
| Benzoyl Peroxide 5% | Acne Treatment | 24 months |
| Coal Tar Extract 2% | Psoriasis Treatment | 36 + months |
| Allantoin .5% | Dry Skin Product | 24-36 months |
| Glycerin 5% | Dry Skin Product | 36 + months |
| Camomile Extract 1% | Anti-itch Product | 18 months |
| Butaben Picrate 1% | Burn Anesthetic | 18-24 months |
| Hydrocortisone .5% | General Steroid | 24-36 months |
| Providone-Iodine 1% | Antiseptic Product | 24-36 months |
| Bactimycin .5% | Antibiotic Product | 24-36 months |
| Diethyltoluamide 1% | Insect Repellent | 24-36 months |
| Papain | Psoriasis Treatment | 24-30 months |
| 13-Cis Retinoic Acid .1% | Acne Treatment | 18-24 months |

(*Note: When formulated in accordance with present invention.)

From Table I, it can be readily seen that the volatile silicone based vehicle system of the present invention provides an excellent matrix for the stabilization of many drugs and cosmetic agents that are known to decompose in aqueous vehicles or easily oxidize in creams and lotions.

The silicone/fatty alcohol ($C_{12}$-$C_{22}$) system of the present invention further offers a vehicle of low-irritancy potential. This is important in treating skin disorders or sensitive skin with any cosmetic agent or drug. Many of the vehicles currently used contain ethyl alcohol, isopropyl alcohol, glycols and other moderately irritating substances. The silicone/fatty alcohol system provides a non-stinging, non-irritating and low allergenic vehicle.

The increased bioavailability of the hydroquinone stick of this disclosure when compared to the more traditional vehicles such as creams and lotions, is a unique result. It is commonly known, in comparing the efficacies of different antiperspirant vehicles, such as creams, aerosols, roll-ons and sticks, that the determining factor is the level of the active ingredient (antiperspirant). That is, the same percentage of active antiperspirant ingredient will produce the same level of antiperspirant effect; regardless of the vehicle used.

As shown in Tables II and III, the present invention demonstrates a substantially improved drug bioavailability, and therefore efficacy, over the other commonly used vehicles containing the same percentage of active ingredient (e.g., hydroquinone). In addition, the present invention demonstrates a substantially greater bioavailability than a standard cream vehicle containing over twice the active ingredient. These results are remarkable in comparison to what would be expected by simply utilizing the prior antiperspirant technology.

In one practice of the present invention using stearyl alcohol, all of the desired ingredients with the exception of the volatile silicone are mixed together and the mixture is then heated gently to about 80° C. until all of the ingredients are thoroughly mixed throughout the melted stearyl alcohol (MP=80° C.). The melted solution or suspension is then cooled to 60°-70° C. and the volatile silicone is added to the cooled mixture and stirred thereinto. When the silicone is thoroughly mixed throughout, the resulting mixture is poured into suitable molds or containers and allowed to cool until solidified. A propitious effect of this practice is that the active ingredient maintains its homogeneous dispersion throughout the solidified mass and there is little or no settling therein.

The invention has been successfully practiced to produce the stick compositions reported below which are then capable of delivering the noted active pharmaceutical and cosmetic ingredient to the desired sites in an easy and efficient manner.

The user employs the resulting stick by grasping the container in which the vehicle with its active ingredient has been disposed. The conventional push-up container, that is, a container having a base plate which is upwardly mobile in response to a force applied thereto by the consumer, which in turn forces the vehicle upwardly until an applicator surface is exposed above the upper rim of the container, can be considered to typify the container used herein. The user then manipulates the container in a stroke-wise fashion to paint the desired location with the mixture thereby delivering the active ingredient to the situs where its action is desired or required. This, of course is not intended to limit the use of the present invention to only stick forms, but is presented as an example of one potential use.

To further aid in the understanding of the present invention, and not by way of limitation, the following examples are presented.

EXAMPLE 1

A batch of a hydroquinone-containing vehicle is prepared to provide a product for the treatment of hyperpigmentation. Note that such a product, to be effective, must be capable of penetrating the epidermis to reach the hyperactive melanocytes positioned at the dermal-/epidermal junction.

A mixture of hydroquinone, benzophenone-3, Octyl Dimethyl-para-amino-benzoic acid, Laureth-4, stearyl alcohol, cetyl alcohol, PEG-1000, and preservatives are stirred together and gently heated to 80° C. where it is maintained while all of the ingredients are thoroughly blended throughout the molten mass. The molten solution/suspension is then cooled to a temperature between 60°-70° C. and a volatile silicone (cyclomethicone) is added thereto and blended therein. After the silicone is thoroughly mixed with all of the other ingredients, the mixture is poured into a cylindrical mold or container and cooled further until it is completely solidified.

The resulting product, herein denominated "hydroquinone stick" has the following analysis (in weight percent):
2.0% Hydroquinone
3.0% Benzophenone-3
7.0% Octyl dimethyl-PABA
4.0% Laureth-4
20.0% Stearyl Alcohol
5.0% Cetyl Alcohol
0.3% Various preservatives
6.0% PEG-1000
52.7% Volatile Silicone

EXAMPLE 2

A hydroquinone stick was prepared according to EXAMPLE I. A product was produced having the following composition (in weight percent):
2.0% Hydroquinone
3.0% Benzophenone-3
7.0% Octyldimethyl PABA
4.0% Ethoxy Ethanol
0.3% Various Preservatives
10.0% PEG-1000
30.0% Stearyl Alcohol
44.7% Volatile Silicone

EXAMPLE 3

The hydroquininone sticks prepared according to Example 1 was tested for bioavailability against the major commercial OTC products sold for skin bleaching using the standard protocol for such tests based on FICK'S Law (see: Franz, T. J., "On the bioavailability of topical formulations..." J.Amer. Academy of Dermatology, St. Louis, Vol 9, No 1, pp 63-73 at 68-69). The results are reported in Table II, and expressed as the percent of the applied dose absorbed over 24 hours.

TABLE II

| Product | Manufacture | Vehicle | % Active | % absorbed in 24 hours |
|---|---|---|---|---|
| Esoterica ® | Norcliff | Cream | 2.0% | 2.5 |
| Porcelana ® | J. Martin Inc. | Cream | 2.0% | 2.0 |
| Faience ® | Lee Pharm. | Lotion | 2.0% | 2.0 |
| Example 1 | | Stick | 2.0% | 28.0 |
| Example 2 | | Stick | 2.0% | 32.0 |

EXAMPLE 4

Repeating the procedure of Example 3, the hydroquininone stick of Example 1 was tested for bioavailability against the major ethical pharmaceutical (Rx) cream for treating skin hyperpigmentation. The results of this test appear in Table III.

TABLE III

| Product | Manufacture | Vehicle | % Active | % absorbed in 24 hours |
|---|---|---|---|---|
| Eldoquin | Elder Pharm. | Cream | 4.0% | 15.0 |
| Example 1 | | Stick | 2.0% | 32.0 |

EXAMPLE 5

A benzoyl peroxide stick was prepared using the procedures described in Example 1. A product was produced having the following composition (in weight percent):
6.4% Benzoyl peroxide-(78% Active)
3.0% Laureth-4
4.0% PEG-1000
23.0% Stearyl Alcohol
6.0% Cetyl Alcohol
0.3% Various preservatives
57.3% Volatile Silicone

EXAMPLE 6

A papain stick was prepared using the procedures described in Example 1. A product was produced having the following composition (in weight percent):
1.2% Papain-750
6.0% PEG-1000
0.3% Preservatives
22.0% Stearyl Alcohol
6.0% Cetyl Alcohol
64.5% Volatile Silicone

EXAMPLE 7

A coal tar stick was prepared using the procedures described in Example 1. A product was produced having the following composition (in weight percent):
2.0% Coal Tar Extract
22.0% Stearyl Alcohol
6.0% Cetyl Alcohol
0.3% Preservatives
6.0% PEG-1000
63.7% Volatile Silicone

EXAMPLE 8

An antibiotic stick (using Bactimycin as the active ingredient) was prepared using the procedures described in Example 1. A product was produced having the following composition (in weight percent):
0.5% Bactimycin
21.0% Stearyl Alcohol
6.0% PEG-1000
0.5% Various preservatives
5.0% Cetyl Alcohol
67.0% Volatile Silicone

EXAMPLE 9

A hydrocortisone stick was prepared using the procedures described in Example 1. A product was produced having the following composition (in weight percent):
0.5% Hydrocortisone
21.0% Stearyl alcohol
5.0% PEG-1000
5.0% Cetyl Alcohol
0.5% Preservatives
0.2% TEA-99%
67.8% Volatile Silicone

EXAMPLE 10

A burn stick (using butaben picrate as the active ingredient) was prepared using the procedures described in Example 1. A product was produced having the following composition (in weight percent):
1.0% Butaben Picrate
21.0% Stearyl Alcohol
6.0% PEG-1000
5.0% Cetyl Alcohol
0.25% Petrolatum
0.3% Preservatives
0.5% Glycerin
66.0% Volatile Silicone

EXAMPLE 11

An anti-itch stick (using camomile extract as the active ingredient) was prepared using the procedures described in Example 1. A product was produced having the following composition (in weight percent):
10.0% Camomile extract
21.0% Stearyl Alcohol
5.0% PEG-1000
1.0% Glycerin
0.3% Preservatives
5.0% Cetyl Alcohol
57.7% Volatile silicone

EXAMPLE 12

An antiseptic stick (using providone-iodine as the active ingredient) was prepared using the procedures described in Example 1. A product was produced having the following composition (in weight percent):
1.0% Providone-Iodine
20.0% Stearyl Alcohol
8.0% PEG-1000
0.5% Preservatives
5.0% Cetyl Alcohol
0.5% Petrolatum
65.0% Volatile Silicone

EXAMPLE 13

A dry skin stick (using glycerin and allantoin as the active ingredients) was prepared using the procedures described in Example 1. A product was produced having the following composition (in weight percent):
5.0% Glycerin
0.5% Allantoin
21.0% Stearyl Alcohol
6.0% PEG-1000
5.0% Cetyl Alcohol
0.3% Preservatives
62.2% Volatile Silicone

EXAMPLE 14

An insect repellent stick (using diethyltoluamide as the active ingredient) was prepared using the procedures described in Example 1. A product was produced having the following composition (in weight percent):
1.0% Diethyltoluamide
21.0% Stearyl alcohol
6.0% PEG-1000
1.0% Glycerin
0.2% TEA-99%
0.3% Preservatives
5.0% Cetyl Alcohol
65.5% Volatile Silicone

EXAMPLE 15

A 13-cis-retinoic acid stick for the treatment of acne, was prepared using the procedure described in Example I. A product having the following composition (in weight percent).
0.10% 13-cis-Retinoic Acid
29.0% Stearyl Alcohol
1.0% Cetyl Alcohol
3.0% Laureth-4
6.0% Peg-1000
60.9% Volatile Silicone From the foregoing it becomes readily apparent that a novel and unique vehicle system has been herein described which delivers active pharmaceutical and cosmetic ingredients in a form wherein the bioavailability and percutaneous absorption are remarkably enhanced and with which the physical disadvantages of prior art systems have been obviated. Of course, such modifications, alterations and adaptations as will readily occur to the skilled artisan confronted with this disclosure are intended within the spirit of the present invention which is limited only by the scope of the claims appended hereto.

Accordingly, what is claimed is:

1. A pharmaceutical preparation having enhanced bioavailability and percutaneous adsorption comprising a mixture containing from about 20% up to about 40% (w/w) fatty alcohol having 12 to 22 carbon atoms or mixtures thereof; from about 30% up to about 60% (w/w) of a volatile silicone; from about 0.1% up to about 10% (w/w) of hydroquinone and from about 1% to about 10% of an ingredient selected from a preservative, an emulsifier or a mixture thereof.

2. A system according to claim 1 in which said fatty alcohol comprises a mixture of stearyl and cetyl alcohol.

3. A system according to claim 1 in which said volatile silicone is cyclomethicone.

4. A system according to claim 1 in which said volatile silicone is dimethicone.

5. A system according to claim 3 in which said fatty alcohol comprises a mixture of stearyl and cetyl alcohol.

6. A system according to claim 4 in which said fatty alcohol comprises a mixture of stearyl and cetyl alcohol.

7. A pharmaceutical preparation for the treatment of hyperpigmentation consisting of from about 0.1% up to about 10% (w/w) of hydroquinone as its essential ingredient, said ingredient dispersed throughout a semi-solid vehicle having from about 20% up to about 40% (w/w) stearyl and cetyl alcohol; from about 30% up to about 60% (w/w) of a volatile silicone; and from about 1% to about 10% w/w of an ingredient selected from a preservative, an emulsifier or a mixture thereof.

8. A pharmaceutical preparation according to claim 7 in which said volatile silicone is cyclomethicone.

* * * * *